US007052696B2

(12) United States Patent
Fields et al.

(10) Patent No.: US 7,052,696 B2
(45) Date of Patent: May 30, 2006

(54) ANTIGENIC EPITOPES AND MOSAIC POLYPEPTIDES OF HEPATITIS C VIRUS PROTEINS

(75) Inventors: Howard A. Fields, Marietta, GA (US); Yury E. Khudyakov, Duluth, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/758,308

(22) Filed: Jan. 10, 2001

(65) Prior Publication Data

US 2002/0090607 A1  Jul. 11, 2002

Related U.S. Application Data

(60) Provisional application No. 60/092,339, filed on Jul. 10, 1998.

(51) Int. Cl.
  *A61K 39/12*  (2006.01)
  *A61K 39/29*  (2006.01)
  *A61K 38/16*  (2006.01)
  *C07K 14/00*  (2006.01)
  *C07K 14/02*  (2006.01)
  *C07K 14/08*  (2006.01)

(52) U.S. Cl. .............................. 424/184.1; 424/185.1; 424/186.1; 424/189.1; 424/199.1; 424/196.11; 424/228.1; 424/9.1; 435/5; 435/7.1; 530/350; 530/300

(58) Field of Classification Search ................ 530/350, 530/300; 424/184.1, 185.1, 186.1, 192.1, 424/228.1, 9.1, 196.11, 199.1, 189.1; 435/5, 435/7.1
See application file for complete search history.

(56) References Cited

U.S. PATENT DOCUMENTS

| 4,683,202 A |   | 7/1987  | Mullis .......................... 435/91 |
|---|---|---|---|
| 4,722,848 A |   | 2/1988  | Paoletti et al. ................. 424/89 |
| 4,946,778 A |   | 8/1990  | Ladner et al. .............. 435/69.6 |
| 5,426,039 A |   | 6/1995  | Wallace et al. ............. 435/91.2 |
| 5,683,864 A | * | 11/1997 | Houghton et al. .............. 435/5 |
| 6,150,087 A |   | 11/2000 | Chien ............................ 435/5 |
| 6,428,792 B1 |  | 8/2002  | Valenzuela et al. ....... 424/228.1 |

FOREIGN PATENT DOCUMENTS

| EP | 0464 287 A1 | * | 8/1992 |
|---|---|---|---|
| EP | 0805 160 A1 | * | 11/1997 |
| JP | 07322881    | * | 5/1994 |
| WO | WO 97/44469 | * | 11/1997 |

OTHER PUBLICATIONS

Chien et al. (a) P.N.A.S. USA. 1992, vol. 89, pp. 10011-10015.*

Chien et al. (b) J. Gastro. Hepto. 1993, vol. 8, pp. S33-S39.*
Kato et al. P.N.A.S. USA. 1990, vol. 87, pp. 9524-9528.*
Jin et al. Arch. Biochem. Biophy. 1995, vol. 323, No. 1, pp. 47-53.*
Barrera et al. Vox Sang 1995, vol. 68, pp. 15-18.*
Hijitkata et al. Proc. Natl. Acad. Sci. USA, 1993, vol. 90, pp. 10773-10777.*
Eisenbraun et al., Examination of Parameters Affecting the Elicitation of Humoral Immune Responses by Particle Bombardment-Mediated Genetic Immunization. *DNA Cell Biol.* 12(9):791-797 (1993).
Miller et al., Vaccination of Rhesus Monkeys with Synthetic Peptide in a Fusogenic Proteoliposome Elicits Simian Immunodeficiency Virus-Specific CD8+ Cytotoxic T lymphocytes. *J. Exp. Med.* 176:1739-1744 (Dec. 1992).
Wolff et al., Long-term persistence of plasmid DNA and foreign gene expression in mouse muscle. *Hum. Mol. Genet.* 1(6):363-369 (1992).
Chien et al., Diagnosis of Hepatitis C Virus (HCV) Infection using an Immunodominant Chimeric Polyprotein to Capture Circulating Antibodies: Reevaluation of the Role of HCV in Liver Disease. *Proc Natl. Acad. Sci. USA* 89:10011-10015 (Nov. 1992).
Tang et al., Genetic immunization is a simple method for eliciting an immune response. *Nature* 356:152-154 (Mar. 12, 1992).
Goodman-Snitkoff et al., Role of intrastructural/intermolecular help in immunization with peptide-phospholipid complexes. *J. Immunol.* 147(2):410-415 (Jul. 15, 1991).
Huse et al., Generation of a Large Combinatorial Library of the Immunoglobulin Repertoire in Phage Lambda. *Science* 246:1275-1281 (Dec. 8, 1989).
Wu et al., Targeting Genes: Delivery and Persistent Expression of a Foreign Gene Driven by Mammalian Regulatory Elements *in Vivo. J. Biol. Chem.* 264(29):16985-16987 (Oct. 15, 1989).

(Continued)

*Primary Examiner*—James Housel
*Assistant Examiner*—Bao Qun Li
(74) *Attorney, Agent, or Firm*—Needle & Rosenberg, PC

(57) ABSTRACT

Antigenic epitopes of hepatitis C virus (HCV) and mosaic HCV polypeptides useful as reagents in assays for the diagnosis or monitoring of HCV in a biological sample. The antigenic epitopes and mosaic polypeptides are also useful for the construction of immunogenic pharmaceutical compositions, such as vaccines. The mosaic polypeptides are artificial composite proteins constructed from diagnostically relevant antigenic regions derived from different HCV proteins. Preferably, the mosaic polypeptides contain antigenic epitopes from the core protein, NS3 protein, and NS4 protein. The preferred mosaic polypeptides optionally contain an additional antigenic epitope from either the NS4 protein or the NS5a protein or both.

8 Claims, No Drawings

OTHER PUBLICATIONS

Ward et al., Binding activities of a repertoire of single immunoglobulin variable domains secreted from *Escherichia coli. Nature* 341:544-546 (Oct. 12, 1989).

Kaneda et al., Increased Expression of DNA Cointroduced with Nuclear Protein in Adult Rat Liver. *Science* 243:375 (Jan. 20, 1989).

Benvenisty et al. Direct introduction of genes into rats and expression of the genes. *Proc. Natl. Acad. Sci. USA* 83:9551-9555 (Dec. 1986).

Seeger et al., The cloned genome of ground squirrel hepatitis virus is infectious in the animal. *Proc Natl. Acad. Sci. USA* 81:5849-5852 (Sep. 1984).

Kearney et al., A new mouse myeloma cell line that has lost immunoglobulin expression but permits the construction of antibody-secreting hybrid cell lines. *J. Immunol.* 123(4):1548-1550 (Oct. 1979).

Kohler et al., Continuous cultures of fused cells secreting antibody of predefined specificity. *Nature* 256:495-497 (Aug. 7, 1975).

Cuatrecasas. Protein Purification by Affinity Chromatography. Derivatizations of agarose and polyacrylamide beads. *J. Biol. Chem.* 245:3059-3065 (Jun. 25, 1970).

Farci, et al., "The Outcome of Acute Hepatitis C Predicted by the Evolution of the Viral Quasispecies," *Science* 288(5464):339-344 (Apr. 14, 2000).

Kumar, et al., "Hepatitis B virus envelope epitopes: gene assembly and expression in *Escherichia coli* of an immunologically reactive novel multiple-epitope polypeptide 1 (MEP-1)," *Gene* 110:137-144 (1992).

Presentation entitled, "Epidemiology and Prevention of Viral Hepatitis A to E: An Overview," Hepatitis Branch, Centers for Disease Control and Prevention, printed from http://www.cdc.gov/ncidod/diseases/hepatitis/slideset/intro/hep_intro.pdf (1 page).

Presentation entitled, "Hepatitis B Virus," Centers for Disease Control and Prevention, printed from http://www.cdc.gov/ncidod/diseases/hepatitis/slideset/hep_b/hep_b.pdf (3 pages).

Presentation entitled, "Hepatitis C," Hepatitis Branch, Centers for Disease Control and Prevention, printed from http://www.cdc.gov/ncidod/diseases/hepatitis/slideset/hep_c/hep_c/hcv_epi_for_distrib_000925.pdf, (dated Sep. 25, 2000), (7 pages).

Presentation entitled, "Hepatitis E Virus," Centers for Disease Control and Prevention, printed from http://www.cdc.gov/ncidod/diseases/hepatitis/slideset/hep_e/hep_e.pdf (1 page).

Website: "30.0.1.0.001 Hepatitis B virus," printed from http://www.ncbi.nlm.nih.gov/ICTVdb/Ictv/index.htm (2 pages).

Website: "ICTVdB Index of Viruses," printed from http://www.ncbi.nlm.nih.gov/ICTVdb/Ictv/index.htm (5 pages).

Website: "ICTVdB Virus Descriptions," printed from http://www.ncbi.nlm.nih.gov/ICTVdb/Ictv/index.htm (12 pages).

Yagi et al., "An Epitope Chimeric Antigen for the Hepatitis C Virus Serological Screening Test," *Biol Pharm Bull* 19(10):1254-1260 (1996).

* cited by examiner

SEQUENCE LISTING

```
<160> NUMBER OF SEQ ID NOS:   5

<210> SEQ ID NO 1
<211> LENGTH: 91
<212> TYPE: PRT
<213> ORGANISM: Hepatitis C Virus

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
        50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met
                85                  90

<210> SEQ ID NO 2
<211> LENGTH: 102
<212> TYPE: PRT
<213> ORGANISM: Hepatitis C Virus

<400> SEQUENCE: 2

Val Pro His Pro Asn Ile Glu Glu Val Ala Leu Ser Asn Thr Gly Glu
1               5                   10                  15

Ile Pro Phe Tyr Gly Lys Ala Ile Pro Ile Glu Ala Ile Lys Gly Gly
                20                  25                  30

Arg His Leu Ile Phe Cys His Ser Lys Lys Lys Cys Asp Glu Leu Ala
            35                  40                  45

Ala Lys Leu Thr Gly Leu Gly Leu Asn Ala Val Ala Tyr Tyr Arg Gly
        50                  55                  60

Leu Asp Val Ser Val Ile Pro Thr Ser Gly Asp Val Val Val Ala Thr
65                  70                  75                  80

Asp Ala Leu Met Thr Gly Phe Thr Gly Asp Phe Asp Ser Val Ile Asp
                85                  90                  95

Cys Asn Thr Cys Val Thr
                100

<210> SEQ ID NO 3
<211> LENGTH: 79
<212> TYPE: PRT
<213> ORGANISM: Hepatitis C Virus
```

-continued

```
<400> SEQUENCE: 3

Ser Val Val Ile Val Gly Arg Ile Ile Leu Ser Gly Arg Pro Ala Val
1               5                   10                  15

Ile Pro Asp Arg Glu Val Leu Tyr Gln Glu Phe Asp Glu Met Glu Glu
            20                  25                  30

Cys Ala Ser His Leu Pro Tyr Ile Glu Gln Gly Met Gln Leu Ala Glu
            35                  40                  45

Gln Phe Lys Gln Lys Ala Leu Gly Leu Leu Gln Thr Ala Thr Lys Gln
        50                  55                  60

Ala Glu Ala Ala Ala Pro Val Val Glu Ser Lys Trp Arg Ala Leu
65                  70                  75

<210> SEQ ID NO 4
<211> LENGTH: 33
<212> TYPE: PRT
<213> ORGANISM: Hepatitis C Virus

<400> SEQUENCE: 4

Met Asn Arg Leu Ile Ala Phe Ala Ser Arg Gly Asn His Val Ser Pro
1               5                   10                  15

Thr His Tyr Val Pro Glu Ser Asp Ala Ala Arg Val Thr Gln Ile
            20                  25                  30

Leu

<210> SEQ ID NO 5
<211> LENGTH: 102
<212> TYPE: PRT
<213> ORGANISM: Hepatitis C Virus

<400> SEQUENCE: 5

Lys Ala Thr Cys Thr Thr His His Asp Ser Pro Asp Ala Asp Leu Ile
1               5                   10                  15

Glu Ala Asn Leu Leu Trp Arg Gln Glu Met Gly Gly Asn Ile Thr Arg
            20                  25                  30

Val Glu Ser Glu Asn Lys Val Val Ile Leu Asp Ser Phe Asp Pro Ile
            35                  40                  45

Arg Ala Val Glu Asp Glu Arg Glu Ile Ser Val Pro Ala Glu Ile Leu
        50                  55                  60

Arg Lys Pro Arg Lys Phe Pro Pro Ala Leu Pro Ile Trp Ala Arg Pro
65                  70                  75                  80

Asp Tyr Asn Pro Pro Leu Leu Glu Ser Trp Lys Asp Pro Asp Tyr Val
                85                  90                  95

Pro Pro Val Val His Gly
            100
```

ANTIGENIC EPITOPES AND MOSAIC POLYPEPTIDES OF HEPATITIS C VIRUS PROTEINS

This application claims priority to PCT/US99/15578 filed Jul. 9, 1999 which claims priority to 60/092,339 filed Jul. 10, 1998 which are both incorporated herein by this reference in their entirety.

TECHNICAL FIELD

The present invention relates to the fields of virology and immunology and more specifically relates to antigenic peptides of the hepatitis C virus (HCV) and the use of the antigenic peptides in an immunoassay for the diagnosis of HCV infection.

BACKGROUND OF THE INVENTION

The hepatitis C virus (HCV) is a major causative agent of parenterally transmitted non-A, non-B hepatitis worldwide. Non-A, non-B hepatitis is now the major form of posttransfusion hepatitis in the United States. The HCV genome consists of a 94 kb positive sense RNA molecule that contains one large open reading frame capable of encoding a polyprotein of 3010 or 3011 amino acids. The HCV structural proteins, especially the nucleocapsid protein, have been found to contain broadly reactive antigenic epitopes.

Currently available assays for diagnosing HCV invention, such as the use of immune electron microscopic techniques to detect virions in feces, lack the specificity and sensitivity to be useful for clinical or epidemiological analysis.

Recently, an HCV antigen was constructed by joining three large segments of proteins (266 mers, 363 mers, and 119 mers) into one polypeptide chain (Chien et al., *Proc. Nat'l Acad. Sci. USA* 89:1011–10015 (1992)). Examples of successful expression of small antigenically active regions with carrier proteins also exist in the literature. However, all of these antigens lack sensitivity.

None of the above-described HCV peptides or recombinant antigens provide a sensitive and specific means for diagnosing HCV infection. Therefore, because of the lack of sensitivity and difficulty of performing the currently available tests, there exists a need for a rapid, simple, and highly sensitive and specific diagnostic test for HCV infection

SUMMARY OF THE INVENTION

Antigenic epitopes of hepatitis C virus (HCV) proteins, mosaic HCV polypeptides, and nucleic acid molecules encoding the antigenic epitopes and mosaic polypeptides are described herein. The antigenic epitopes and mosaic HCV polypeptides are useful as reagents in assays for the detection of HCV infection in a patient sample. The nucleic acid molecules encoding the antigenic epitopes and mosaic polypeptides are useful for the production thereof by recombinant means. The mosaic polypeptides are artificial composite proteins constructed from diagnostically relevant antigenic regions derived from different HCV proteins.

Preferably, the mosaic polypeptides contain antigenic epitopes from the core protein, NS3 protein, and NS4 protein. The preferred mosaic polypeptides optionally contain an additional antigenic epitope from either the NS4 protein or the NS5a protein or both.

Most preferably, the antigenic epitope of the core protein contains amino acid residues 1–91 of the HCV polyprotein (SEQ ID NO:1); the antigenic epitope of the NS3 protein contains amino acid residues 1471–1573 of the HCV polyprotein (SEQ ID NO:2); the antigenic epitope of the preferred NS4 protein contains amino acid residues 1789–1867 of the HCV polyprotein (SEQ ID NO:3); the antigenic epitope of the optional NS4 protein contains amino acid residues 1916–1948 of the HCV polyprotein (SEQ ID NO:4); and the antigenic epitope of the optional NS5a protein contains amino acid residues 2322–2423 of the HCV polyprotein (SEQ ID NO:5). The antigenic epitopes can be placed in any order within the mosaic polyprotein.

The antigenic epitopes and mosaic polypeptides are useful as reagents in assays, such as immunoassays, for the diagnosis or monitoring of HCV infection in a patient sample. Preferably, the antigenic epitopes and mosaic polypeptides bind to antibodies present in the biological sample being tested. The detection of antigenic epitopes or mosaic polypeptides bound to antibodies indicates that the human or animal from whom the biological sample was taken is infected with HCV.

The antigenic epitopes and mosaic polypeptides are also useful for the construction of pharmaceutical compositions, such as vaccines, comprising an immunogenic amount of the antigenic epitope or mosaic polypeptide and a pharmaceutically acceptable carrier. The pharmaceutical compositions are administered to humans or animals to prevent, minimize or reduce HCV infection, particularly to patients who have been exposed to HCV or to individuals, such as health care workers or blood products recipients, who are more likely to become exposed to HCV infection.

The antigenic epitopes and mosaic polypeptides are additionally useful for the generation of antibodies, both monoclonal and polyclonal, that are reactive with and can be used to detect HCV proteins in a sample. Such antibodies are particularly useful for laboratory research purposes to study HCV.

Kits for the detection of HCV in a biological sample are also provided. The kits contain one or more of the antigenic epitopes or mosaic polypeptides. The kits may optionally contain an apparatus and one or more containers for obtaining and storing the sample prior to and during analysis and suitable buffers and other reagents to facilitate antibody-antigen binding and detection. Each component of each kit may be provided in separate containers or any combination of the components may be provided in a single container.

Therefore, it is an object of the present invention to provide methods for detecting HCV in a biological sample, wherein the methods have high specificity for HCV.

It is a further object of the present invention to provide methods for detecting HCV that are rapid, simple, reliable, sensitive, and not labor intensive.

It is a further object of the present invention to provide an assay for HCV in which only a small amount of sample is needed for highly sensitive analysis.

These and other objects, features, and advantages of the present compositions, methods and kits will become apparent after a review of the following detailed description of the disclosed embodiments and the appended claims.

DETAILED DESCRIPTION OF THE DISCLOSED EMBODIMENTS

Antigenic epitopes or peptides of hepatitis C virus (HCV) proteins, mosaic HCV polypeptides, nucleic acid molecules encoding the antigenic epitopes and mosaic polypeptides, pharmaceutical compositions and kits containing the antigenic epitopes and mosaic polypeptides, and antibodies specifically immunoreactive with the antigenic epitopes and mosaic polypeptides are provided. The mosaic polypeptides are artificial composite proteins constructed from diagnostically relevant antigenic regions derived from different HCV proteins. The antigenic epitopes, mosaic polypeptides and antibodies thereto are useful as reagents in assays for the detection of HCV infection in a biological sample, such as a patient sample. The nucleic acid molecules encoding the antigenic epitopes and mosaic polypeptides are useful for the production of the antigenic epitopes and mosaic polypeptides.

Preferably, the mosaic polypeptides contain antigenic epitopes from the core protein, NS3 protein, and NS4 protein. Additional HCV proteins may also be included. The preferred mosaic polypeptides optionally contain an additional antigenic epitope from either the NS4 protein or the NS5a protein or both the NS4 protein and the NS5a protein. The preferred HCV genotype is genotype 1b.

The antigenic epitope peptides are fused into a single mosaic polypeptide by recombinant or synthetic techniques. In recombinant procedures, mosaic proteins are made by ligating synthetic or recombinant nucleic acids which encode the antigenic epitopes. These nucleic acids are ligated enzymatically (e.g., using a DNA Ligase enzyme) or synthetically. Alternatively, a single nucleic acid can be synthesized which encodes multiple antigenic epitope peptides. In either case, the resulting nucleic acid encodes multiple antigenic epitope peptides, all in the same reading frame. Thus, the translated polypeptide comprises antigenic epitope peptide domains.

When the mosaic polypeptides are produced by automated chemical synthetic procedures, concatamers of peptides are coupled directly. This is performed chemically by joining peptides using standard chemical methods. Alternatively, a polypeptide can be synthetically produced having an amino acid sequence that encodes multiple immunogenic peptides.

Chemical or recombinant linker regions are optionally included between the immunogenic peptide domains to facilitate presentation of the domains to antibodies which bind the domains. In preferred embodiments, ten to fifty amino acids are inserted between immunogenic domains. Essentially any amino acid, or chemical moiety which forms amide and carboxyl linkages can be used as a linker.

Most preferably, the antigenic epitope or peptide of the core protein contains amino acid residues 1–91 of the HCV polyprotein (SEQ ID NO:1); the antigenic epitope or peptide of the NS3 (non-structural) protein contains amino acid residues 1471–1573 of the HCV polyprotein (SEQ ID NO:2); the antigenic epitope or peptide of the preferred NS4 protein contains amino acid residues 1789–1867 of the HCV polyprotein (SEQ ID NO:3); the antigenic epitope or peptide of the optional NS4 protein contains amino acid residues 1916–1948 of the HCV polyprotein (SEQ ID NO:4); and the antigenic epitope or peptide of the optional NS5a protein contains amino acid residues 2322–2423 of the HCV polyprotein (SEQ ID NO:5). The antigenic epitopes can be placed in any order within the mosaic polyprotein.

The preferred antigenic epitope of the core protein, containing amino acid residues 1–91 of the HCV polyprotein (SEQ ID NO: 1), is as follows:
MSTNPKPQRKTKRNTNRRPQDVKFPGGG-
   QIVGGVYLLPRR GPRLGVRATRKTSERSQPRGR-
   RQPIPKARRPEGRTWAQPGY PWPLYGNEGM The preferred antigenic epitope of the NS3 protein, containing amino acid residues 1471–1573 of the HCV polyprotein (SEQ ID NO:2), is as follows:
VPHPNIEEVALSNTGEIPFYGKAIP-
   IEAIKGGRHLIFCHSKKKC DELAAKLT-
   GLGLNAVAYYRGLDVSVIPTSGDVVVATDALM
   TGFTGDFDSVIDCNTCVT The preferred antigenic epitope of the NS4 protein, containing amino acid residues 1789–1867 of the HCV polyprotein (SEQ ID NO:3), is as follows:
SVVIVGRIILSGRPAVIPDREVLYQEF-
   DEMEECASHLPYIEQG MQLAEQFKQKAL-
   GLLQTATKQAEAAAPVVESKWRAL The preferred antigenic epitope of the optional NS4 protein, containing amino acid residues 1916–1948 of the HCV polyprotein (SEQ ID NO:4), is as follows:
MNRLIAFASRGNHVSPTHYVPESDAAARVTQIL The preferred antigenic epitope of the optional NS5a protein, containing amino acid residues 2322–2423 of the HCV polyprotein (SEQ ID NO:5), is as follows:
KATCTHHDSPDADLIEANLLWRQEMGG-
   NITRVESENKVVI LDSFDPIRAVEDEREISVPAEIL-
   RKPRKFPPALPIWARPDYNP PLLESWKDPDYVPPV-
   VHG It will be understood by those skilled in the art that the antigenic epitopes alone or antigenic epitopes that are recombinantly or synthetically combined to produce the mosaic polypeptides specifically include amino acid sequences containing conservative amino acid substitutions of the foregoing sequences. In such sequences, one or a few amino acids of one or more of the foregoing amino acid sequences are substituted with different amino acids having highly similar properties. The replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Definitions

The terms "a", "an" and "the" as used herein are defined to mean one or more and include the plural unless the context is inappropriate.

"Peptides," "polypeptides" and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at tie amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the mosaic polypeptides to which the phrase refers. Thus, the description of a peptide "consisting essentially of . . . " excludes any amino acid substitutions, additions, or deletions that would substantially alter the biological activity of that peptide.

The word "antigen", as used herein, refers to an entity or fragment thereof which can induce an immune response in a mammal. The term includes immunogens and regions responsible for antigenicity or antigenic determinants.

The term "antigenic determinant" or "antigenic epitope" refers to a peptide or region of an HCV protein recognized by an antibody, e.g., in serum raised against wild-type HCV.

The phrases "specifically binds to a peptide" or "specifically immunoreactive with", when referring to an antibody, refer to a binding reaction which is determinative of the presence of a peptide in the presence of a heterogeneous population of proteins and other biological substances. Under designated immunoassay conditions, the specified antibodies bind preferentially to a particular peptide and do not bind in a significant amount to other proteins present in the sample. Specific binding to a peptide under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein.

The terms "nucleic acid" or "nucleic acid molecule", as used herein, refer to a deoxyribonucleotide (DNA) or ribonucleotide (RNA) in either single- or double-stranded form, and unless otherwise limited, encompass known analogs of natural nucleotides which can function in a manner similar to the naturally occurring nucleotides.

The phrase "nucleic acid sequence encoding" refers to a nucleic acid sequence which directs the expression of a specific protein or peptide. The nucleic acid sequence includes both the DNA sequence that is transcribed into RNA and the RNA sequence that is translated into the protein. The nucleic acid sequence includes both the full length nucleic acid sequence as well as any non-full length sequences derived from the full length sequence. It will be understood by those of skill that the sequence includes the degenerate codons of the native sequence or sequences which may be introduced to provide codon preference in a specific host cell.

The phrase "conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given peptide. Such nucleic acid variations are silent variations, which are one species of conservatively modified variations. One of skill will recognize that each codon in a nucleic acid (except AUG, which is ordinarily the only codon for methionine) can be modified to yield a functionally identical molecule by standard techniques. Accordingly, each silent variation of a nucleic acid which encodes a peptide is implicit in any described amino acid sequence. Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The term "substantial identity" means that a polypeptide comprises a sequence that has at least 80% sequence identity, preferably 90%, more preferably 95% or more, compared to a reference sequence over a comparison window of about 10 to about 20. Another indication that polypeptide sequences are substantially identical is if one peptide is immunologically reactive with antibodies raised against the other peptide. Thus, the mosaic polypeptides described herein include peptides immunologically reactive with antibodies raised against the disclosed mosaic polypeptides.

The phrases "isolated" or "biologically pure" refer to material which is substantially or essentially free from components which normally accompany it as found in its native state. Thus, the mosaic polypeptides described herein do not contain materials normally associated with their in situ environment, e.g., other proteins from a merozoite membrane. Typically, the isolated, immunogenic HCV mosaic polypeptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

The term "residue" refers to an amino acid (D or L) or an amino acid mimetic incorporated in a oligopeptide by an amide bond or amide bond mimetic. An amide bond mimetic includes peptide backbone modifications well known to those skilled in the art.

HCV Immunoassays

The antigenic epitopes, mosaic polypeptides, and antibodies specifically immunoreactive with the antigenic epitopes or mosaic polypeptides, prepared as described in more detail below, are useful as reagents in assays, such as immunoassays, for the diagnosis or monitoring of HCV infection in a biological sample. In a preferred embodiment, the antigenic epitope or mosaic polypeptide binds to antibodies present in the biological sample being tested. In an alternative preferred embodiment, antibodies specifically immunoreactive with the antigenic epitopes or mosaic polypeptides bind to HCV proteins present in the biological sample being tested In accordance with the method, the antigenic epitope or mosaic polypeptide or antibody thereto is combined with a biological sample under conditions that promote or enhance the specific binding of analyte to antibody to form an analyte-antibody complex. For example, the antigenic epitope, mosaic polypeptide or antibody thereto is combined in a solution, such as a buffer solution, with the sample to be analyzed, and the solution is incubated or reacted for a sufficient amount of time under conditions that allow the binding of antibody to analyte. The reaction mixture is then analyzed for the presence of analyte-antibody complexes, either by detecting the complexes, by detecting a labeled component of the complexes, or by detecting a reagent that binds to the complexes such as an anti-idiotypic antibody or fragment thereof. The complexes may be separated from the unreacted components of the assay, using methods such as filtration, centrifugation, or solid phase capture, to facilitate or enhance detection.

Throughout the assay, incubation and/or washing steps may be required after each combination of reagents. Incubation steps can vary from about five seconds to several hours, preferably from about five minutes to about 24 hours. However, the incubation time will depend upon the assay format, analyte, volume of solution, concentrations, and the like. Usually, the assay is carried out at ambient temperature, although assays can be conducted over a range of temperatures, such as 5° C. to 45° C.

Analyte-antibody complexes are detected either visually with the naked eye or by using a conventional detector, such as a colorimeter or reflectometer, which are well known to those skilled in the art. Exemplary immunoassay formats include the competitive immunoassay format, in which labeled an unlabeled reagents compete for the binding partner and the sandwich immunoassay format in which an analyte is captured by a first antibody and detected with a second antibody. A format in which the binding of analyte to antibody and the detection of the analyte-antibody complex are combined is preferred when simplicity and speed are desired elements of the immunoassay.

The detection of antigenic epitopes or mosaic polypeptides bound to antibodies, or the detection of antibodies specifically immunoreactive with the antigenic epitopes or mosaic polypeptides being bound to protein, indicates that the human or animal from whom the biological sample was taken is infected with HCV. A determination of the quantity of antibodies or protein present in the biological sample may be indicative of the severity of the disease or the response to treatment.

The sample to be tested or analyzed may be obtained from any biological source and is preferably taken from a human or animal capable of being infected with or harboring the hepatitis C virus. For example, the sample may be a cell sample, tissue sample or biological fluid, such as whole blood, blood serum, blood plasma, urine, semen, saliva, sputum, cerebrospinal fluid, lacrimal fluid, fermentation fluid, lymph fluid, tissue culture fluid, ascites fluid, synovial fluid, pleural fluid, and the like. The preferred biological sample is a biological fluid from which cells can be removed. The most preferred samples are blood plasma or serum. The biological sample may also be a laboratory research sample such as a cell culture supernatant, viral isolate or viral concentrate. The sample is collected or obtained using methods well known to those skilled in the art.

Although the sample is typically taken from a human patient, the assay can be used to detect antibodies or HCV proteins in samples taken from eukaryotes in general and, in particular, mammals, such as dogs; cats; sheep; cattle; pigs; primates, such as humans, chimpanzees, gorillas, macaques, and baboons; and rodents, such as mice, rats, and guinea pigs.

The sample may be diluted, purified, concentrated, filtered, dissolved, suspended or otherwise manipulated prior to use in the assay. Preferably, a sample containing particulate matter is diluted, filtered, or both diluted and filtered prior to use. The preferred diluent is a buffer solution. Any of a number of standard aqueous buffer solutions, employing one of a variety of buffers, such as phosphate, TRIS detergent, or the like, at physiological pH can be used.

The sample size for the biological fluid sample is preferably between approximately 0.5 µl and 1 ml. A preferred biological fluid sample size is between approximately 1 and 100 µl. Most preferably, the volume of the biological fluid sample is approximately 10 to 50 µl.

Preferably, antibodies in the sample immunoreactive with the antigenic epitope or mosaic polypeptide are detected and quantified by any of a number of means well known to those of skill in the art. Alternatively, HCV proteins or peptides in the sample immunoreactive with antibodies, specific for the antigenic epitopes or mosaic polypeptides, are detected and quantified by the same or similar means well known to those of skill in the art. These methods include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitation reactions, immunodiffusion (single or double), immunoelectrophoresis, radioimmunoassays (RIAs), enzyme-linked immunosorbent assays (ELISAs), immunofluorescent assays, and the like.

One of skill in the art will appreciate that it is often desirable to reduce non-specific binding in immunoassays. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition prior to introduction of the sample to the other immunoassay components. In particular, protein compositions such as bovine serum albumin (BSA), nonfat powdered milk, and gelatin are widely used.

Western blot analysis can also be used to detect and quantify the presence of an HCV peptide in the sample. The technique generally comprises separating sample products by gel electrophoresis on the basis of molecular weight, transferring the separated proteins to a suitable solid support (such as a nitrocellulose filter, a nylon filter, or derivatized nylon filter), and incubating the sample with the antibodies that specifically bind immunogenic HCV peptides. The anti-peptide antibodies specifically bind to a peptide fixed on the solid support. These antibodies are directly labeled or, alternatively, they may be subsequently detected using labeled antibodies (e.g., labeled sheep anti-mouse antibodies where the antibody to a peptide is a murine antibody) that specifically bind to the anti-peptide antibody.

Other assay formats include liposome immunoassays (LIAs), which use liposomes designed to bind specific molecules (e.g., antibodies) and release encapsulated reagents or markers. The released chemicals are then detected according to standard techniques (see, Monroe et al., (1986) Amer. Clin. Prod. Rev. 5:34–41).

The detection of antibodies or peptides in the sample is facilitated by labeling the antigenic epitope, mosaic polypeptide, antibodies specifically immunoreactive with the antigenic epitope or mosaic polypeptide, antibodies specific for the anti-mosaic polypeptide or anti-antigenic epitope antibodies or a complex or combination of epitopes, polypeptides, antibodies or antibody fragments with a labeling agent. Detection may proceed by any known method, such as immunoblotting, western analysis, gelmobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the immunoassay. The detectable group can be any material having a detectable physical or chemical property. Such detectable labels have been well-developed in the field of immunoassays and, in general, any label useful in such methods can be applied in the present method. Thus, a label is any composition detectable by spectroscopic, photochemical, biochemical, immunochemical, electrical, optical or chemical means. Useful labels include magnetic beads; fluorescent dyes, such as fluorescein isothiocyanate, Texas red, rhodamine, and the like; radiolabels such as $^3$H, $^{125}$I, $^{131}$I, $^{35}$S, $^{14}$C or $^{32}$P, enzymes such as LacZ, CAT, horse radish peroxidase, alkaline phosphatase and others commonly used as detectable enzymes, either in an enzyme immunoassay (EIA) or in an enzyme linked immunosorbent assay (ELISA); and calorimetric labels such as colloidal gold or colored glass or plastic, such as polystyrene, polypropylene, or latex beads. The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The antigenic epitopes, mosaic polypeptides or antibodies thereto can also be conjugated directly to signal generating compounds, such as by conjugation to an enzyme or fluorophore. Enzymes of interest as labels will preferably be hydrolases, particularly phosphatases, esterases and glycosidases, or oxidoreductases, particularly peroxidases. Fluorescent compounds, also referred to as fluorogens, include fluorescein and its derivatives, rhodamine and its derivatives, dansyl, umbelliferone, phycoerythrin, allo-phycocyanin, phycocyanin, Texas Red, etc. The fluorogens are generally detected by a fluorescence detector. Chemiluminescent compounds or bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Chemiluminescent compounds such as 2,3-dihydrophthalazinediones, e.g., luminol can also be used. For a review of various labeling or signal producing systems which may be used, see, U.S. Pat. No. 4,391,904.

Additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using ELISAs or by detecting a color change with the aid of a spectrophotometer. In addition, the antigenic epitope or mosaic polypeptide may be labeled with colloidal gold for use in immunoelectron microscopy in accordance with methods well known to those skilled in the art.

Means for detecting labels are well known to those of skill in the art. Thus, for example, where the label is a radioactive label, means for detection include a scintillation counter or photographic film as in autoradiography or gamma ray spectrometry. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels are detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of target antibodies. In this case, mosaic polypeptide-coated particles are agglutinated by samples containing the target antibodies. In this format, none of the components need be labeled and the presence of the target antibody is detected by simple visual inspection.

As mentioned above, depending upon the assay format, various components, including the antigenic epitope, mosaic polypeptide, anti-mosaic polypeptide or anti-antigenic epitope antibody, or anti-idiotypic antibody, may be bound to a solid surface. Many methods for immobilizing biomolecules to a variety of solid surfaces are known in the art. For instance, the solid surface may be a membrane such as nitrocellulose; a microtiter dish such as polyvinyl chloride (PVC), polypropylene, or polystyrene; a test tube such as a glass or plastic test tube; a dipstick made of a material such as glass, PVC, polypropylene, polystyrene, latex, and the like; a microcentrifuge tube; or a glass, silica, plastic, metallic or polymer bead. The desired component may be covalently bound, or noncovalently attached through non-specific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12–24 carbon atoms) alkyl ammonium salts and the like are also suitable. Where the solid surface is porous, various pore sizes may be employed depending upon the nature of the system.

In preparing the surface, a plurality of different materials may be employed such as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes,* chiro Chibata, Halsted Press, New York, 1978, and Cuatrecasas, *J. Biol. Chem.* 245 3059 (1970).

In a preferred embodiment of the immunoassay method, the analyte-antibody complex is detected using a labeled third moiety, such as another antibody, that specifically binds to the analyte-antibody complex, or to a modified capture group (e.g., biotin) which is covalently linked to the analyte or anti-analyte antibody.

Preferably, the labeling agent is an antibody that specifically binds to the capture agent, which would be the antigenic epitope, mosaic polypeptide or antibodies thereto. Such labeling agents are well known to those of skill in the art, and most typically comprise labeled antibodies that specifically bind antibodies of the particular animal species from which the capture agent is derived (e.g., an anti-idiotypic antibody), or antibodies against a peptide when the antigenic epitope is the capture agent. Thus, for example, where the capture agent is a mouse derived anti-peptide antibody, the label agent may be a goat anti-mouse IgG, i.e., an antibody specific to the constant region of the mouse antibody.

Other proteins capable of specifically binding immunoglobulin constant regions, such as streptococcal protein A or protein G are also used as the labeling agent. These proteins are normal constituents of the cell walls of streptococcal bacteria, and exhibit a strong non-immunogenic reactivity with immunoglobulin constant regions from a variety of species.

Immunoassays for detecting a peptide or an antibody to a peptide may be either competitive or noncompetitive. Noncompetitive immunoassays are assays in which the amount of captured analyte (e.g., antigenic epitope, mosaic polypeptide or anti-peptide antibody) is directly measured. In one preferred "sandwich" assay, for example, the capture agent is bound directly to a solid substrate where it is immobilized. If, for example, the capture agent is an antigenic epitope of HCV, these immobilized peptides capture antibodies present in a test sample, such as blood serum. The antibody thus immobilized, or captured, is then bound by a labeling agent, such as a second antibody bearing a label. Alternatively, the second antibody may lack a label, but it may, in turn, be bound by a labeled third antibody specific to antibodies of the species from which the second antibody is derived.

Sandwich assays for a peptide or antibody can also be constructed. As described above, the immobilized peptide specifically binds to the antibody present in the sample. A labeled antibody then binds to the already bound antibody. Free labeled antibody is washed away and the remaining bound labeled antibody is detected (e.g., using a gamma detector where the label is radioactive).

In competitive assays, the amount of analyte (e.g., immunogenic peptide or antibody to an immunogenic peptide) present in the sample is measured indirectly by measuring the amount of an added (exogenous) analyte displaced (or competed away) from a capture agent (e.g., an antibody or peptide) by the analyte present in the sample. In one competitive assay, a known amount of analyte is added to the sample and the sample is contacted with a capture agent, such as a peptide that specifically binds the analyte. The amount of analyte bound to the peptide is inversely proportional to the concentration of analyte present in the sample.

In a preferred embodiment, the capture agent (the antigenic epitope, mosaic polypeptide or antibodies thereto) is immobilized on a solid substrate. The amount of analyte bound to the capture agent is determined either by measuring the amount of antibody present in an antibody/peptide complex or, alternatively, by measuring the amount of remaining uncomplexed antibody. The amount of peptide in a sample to be assayed can also be detected by providing exogenous labeled peptide to the assay.

A hapten inhibition assay is another preferred competitive assay. In this assay, a known analyte, in this case an immunogenic peptide, is immobilized on a solid substrate. A known amount of anti-peptide antibody is added to the sample, and the sample is then contacted with the immobilized peptide. In this case, the amount of antibody bound to the immobilized marker gene polypeptide is proportional to the amount of peptide present in the sample. Again the amount of immobilized antibody is detected by quantitating either the immobilized fraction of antibody or the fraction of the antibody that remains in solution. Detection may be direct where the antibody is labeled, or indirect where a labeled moiety is subsequently added which specifically binds to the antibody as described above. One of skill in the art will appreciate that the role of the peptide and antibody can be reversed to achieve the same effect for the quantitation of the antibody.

Antigenic Epitope Peptide and Mosaic Polypeptide Production

Because the antigenic epitope peptides and mosaic polypeptides described herein are relatively short in length, they can be prepared using any of a number of chemical peptide synthesis techniques well known to those of ordinary skill in the art including both solution methods and solid phase methods, with solid phase synthesis being presently preferred.

The antigenic epitope peptides and mosaic polypeptides can be prepared by recombinant techniques by determining the nucleic acid sequence encoding the amino acid sequences set forth above, inserting the sequences into an expression vector, and expressing the vector in accordance with methods well known to those skilled in the art. Examples of appropriate cloning and sequencing techniques, and instructions sufficient to direct persons of skill through many cloning exercises are found in Sambrook et al. (1989) *Molecular Cloning—A Laboratory Manual* (2nd ed.) Vol. 1–3, Cold Spring Harbor Laboratory, Cold Spring Harbor Press, NY, which is incorporated by reference herein. Product information from manufacturers of biological reagents and experimental equipment also provide information useful in known biological methods.

The nucleic acid molecules encoding the antigenic epitope peptides and mosaic polypeptides, whether RNA, DNA, or cDNA, are isolated from biological sources or synthesized in vitro. The nucleic acid molecules are present in transformed or transfected whole cells, in transformed or transfected cell lysates, or in a partially purified or substantially pure form.

In vitro amplification techniques suitable for amplifying sequences for generating nucleic acid fragments for subsequent subcloning are known. Examples of techniques sufficient to direct persons of skill through such in vitro amplification methods, including the polymerase chain reaction (PCR) the ligase chain reaction (LCR), Q-beta-replicase amplification and other RNA polymerase mediated techniques (e.g., NASBA) are found in Sambrook (above), as well as U.S. Pat. No. 4,683,202 to Mullis et al., and other sources well known to those skilled in the art. Improved methods of cloning in vitro amplified nucleic acids are described in U.S. Pat. No. 5,426,039 to Wallace et al.

Small nucleic acids (less than 100 nucleotides in length) can be synthesized chemically according to the solid phase phosphoramidite triester method using an automated synthesizer. Nucleic acids can also be custom made and ordered from a variety of commercial sources known to persons of skill. Purification, where necessary, is typically performed by either native acrylamide gel electrophoresis or by anion-exchange HPLC.

When the antigenic epitope peptides and mosaic polypeptides are relatively short in length (i.e., less than about 50 amino acids), they are often synthesized using standard chemical peptide synthesis techniques. Each mosaic polypeptide is preferably synthesized as a single contiguous polypeptide. Alternatively, the peptides of the mosaic polypeptide can be synthesized separately and then fused chemically into a single contiguous polypeptide.

Solid phase synthesis in which the C-terminal amino acid of the sequence is attached to an insoluble support followed by sequential addition of the remaining amino acids in the sequence is a preferred method for the chemical synthesis of the antigenic epitopes and mosaic polypeptides described herein. Techniques for solid phase synthesis are known to those skilled in the art.

Alternatively, the antigenic epitopes and mosaic polypeptide described herein are synthesized using recombinant nucleic acid methodology. Generally, this involves creating a nucleic acid sequence that encodes the peptide or polypeptide, placing the nucleic acid in an expression cassette under the control of a particular promoter, expressing the peptide or polypeptide in a host, isolating the expressed peptide or polypeptide and, if required, renaturing the peptide or polypeptide. Techniques sufficient to guide one of skill through such procedures are found in the literature.

While the antigenic epitopes of the mosaic polypeptides are often joined directly together, one of skill will appreciate that the molecules may be separated by a spacer molecule such as, for example, a peptide, consisting of one or more amino acids. Generally, the spacer will have no specific biological activity other than to join the antigenic epitopes together, or to preserve some minimum distance or other spatial relationship between them. However, the constituent amino acids of the spacer may be selected to influence some property of the molecule such as the folding, net charge, or hydrophobicity.

Once expressed, recombinant peptides or polypeptides can be purified according to standard procedures, including ammonium sulfate precipitation, affinity columns, column chromatography, gel electrophoresis and the like. Substantially pure compositions of about 50 to 95% homogeneity are preferred, and 80 to 95% or greater homogeneity are most preferred for use as therapeutic agents.

One of skill in the art will recognize that after chemical synthesis, biological expression or purification, the antigenic epitopes or mosaic polypeptides may possess a conformation substantially different than the native conformations of the constituent peptides. In this case, it is often necessary to denature and reduce polypeptide and then to cause the polypeptide to re-fold into the preferred conformation. Methods of reducing and denaturing proteins and inducing re-folding are well known to those of skill in the art.

Nucleic Acid Sequences

The amino acid sequences of the antigenic epitopes and mosaic polypeptides disclosed herein also provide corresponding nucleic acids which encode the given peptides. Provided with an amino acid sequence of a peptide, one of skill will recognize a variety of equivalent nucleic acids which encode the peptide. This is because the genetic code requires that each amino acid residue in a peptide is specified by at least one triplet of nucleotides in a nucleic acid which encodes the peptide. Due to the degeneracy of the genetic code, many amino acids are equivalently coded by more than one triplet of nucleotides. For instance, the triplets CGU, CGC, CGA, CGG, AGA, and AGG all encode the amino acid Arginine. Thus, at every position where an Arginine is to be encoded by a nucleic acid triplet, the nucleic acid has any of the triplets which encode Arginine. One of skill is thoroughly familiar with the genetic code and its use.

Although any nucleic acid triplet which encodes an amino acid can be used to specify the position of the amino acid in a peptide, certain codons are preferred. It is desirable to select codons for elevated expression of an encoded peptide, for example, when the peptide is purified for use as an immunogenic reagent. Codons are selected by reference to species codon bias tables, which show which codons are most typically used by the organism in which the peptide is to be expressed. The codons used frequently by an organism are translated by the more abundant t-RNAs in the cells of the organism. Because the t-RNAs are abundant, translation of the nucleic acid into a peptide by the cellular translation machinery is facilitated. Codon bias tables are available for most organisms.

Anti-Antigenic Epitope and Anti-Mosaic Polypeptide Antibodies

The antigenic epitopes and mosaic polypeptides are useful for the generation of antibodies, both monoclonal and polyclonal, that are reactive with and can be used to detect HCV proteins or peptides in a sample. Such antibodies are particularly useful for laboratory research purposes as scientific research tools to study HCV, thereby promoting an understanding of the mechanisms of viral pathology and the development of antiviral therapies. The antibodies can be labeled or conjugated as described above. In addition, the peptides can be used to screen antisera from hyperimmune patients from whom can be derived antibodies having a very high affinity for the peptides.

The terms "antibody" or "antibodies" as used herein include monoclonal antibodies, polyclonal, chimeric, single chain, bispecific, simianized, and humanized antibodies as well as Fab fragments, including the products of an Fab immunoglobulin expression library.

Antibodies are raised to the antigenic epitopes and mosaic polypeptides, including individual, allelic, strain, or species variants, and fragments thereof, both in their naturally occurring (full-length) forms and in recombinant forms. Additionally, antibodies are raised to these peptides in either their native configurations or in non-native configurations. Anti-idiotypic antibodies can also be generated. Many methods of making antibodies are known to persons skilled in the art. The following discussion is presented as a general overview of the techniques available; however, one of skill will recognize that many variations upon the following methods are known.

A number of immunogens are used to produce antibodies specifically reactive with peptides. Recombinant or synthetic peptides of ten amino acids in length, or greater, selected from sub-sequences of the antigenic epitopes and mosaic polypeptides disclosed herein are the preferred peptide immunogens for the production of monoclonal or polyclonal antibodies. In one class of preferred embodiments, an immunogenic peptide conjugate is also included as an immunogen. Naturally occurring peptides are also used either in pure or impure form.

Recombinant peptides are expressed in eukaryotic or prokaryotic cells and purified using standard techniques. The peptide, or a synthetic version thereof, is then injected into an animal capable of producing antibodies. Either monoclonal or polyclonal antibodies can be generated for subsequent use in immunoassays to measure the presence and quantity of the peptide.

Methods of producing polyclonal antibodies are known to those of skill in the art. In brief, an immunogen, preferably a purified peptide, a peptide coupled to an appropriate carrier (e.g., GST, keyhole limpet hemanocyanin, etc.), or a peptide incorporated into an immunization vector such as a recombinant vaccinia virus (see, U.S. Pat. No. 4,722,848, which is incorporated by reference herein) is mixed with an adjuvant and animals are immunized with the mixture. The animal's immune response to the immunogen preparation is monitored by taking test bleeds and determining the titer of reactivity to the peptide of interest. When appropriately high titers of antibody to the immunogen are obtained, blood is collected from the animal and antisera are prepared. Further fractionation of the antisera to enrich for antibodies reactive to the peptide is performed where desired. For example, the sera can be titered against the antigenic peptides or mosaic polypeptides in an immunoassay, for example, a solid phase immunoassay with the peptide immobilized on a solid support. Polyclonal antisera with a titer of $10^4$ or greater are selected and tested for their cross reactivity against any known protein, using a competitive binding immunoassay. For example, the antigenic peptide or mosaic polypeptide is immobilized to a solid support. Proteins added to the assay compete with the binding of the antisera to the immobilized antigen. The ability of the above peptides to compete with the binding of the antisera to the immobilized protein is compared to the antigenic peptide or mosaic polypeptide. The percent crossreactivity for the above peptides is calculated, using standard calculations. Those antisera with less than 10% crossreactivity with selected competitor peptides are selected and pooled. The cross-reacting antibodies are then removed from the pooled antisera by immunoabsorbtion with the competitor proteins. Preferably the antisera is selected to have low crossreactivity against known peptides, and any such crossreactivity is removed by immunoabsorbtion prior to use in an immunoassay.

The immunoabsorbed and pooled antisera are then used in a competitive binding immunoassay to compare the binding of a test peptide to the antigenic epitope or mosaic polypeptides. In order to make this comparison, the two peptides are each assayed at a wide range of concentrations and the amount of each peptide required to inhibit 50% of the binding of the antisera to the immobilized is determined using standard techniques. If the amount of the test peptide required is less than twice the amount of the antigenic epitope or mosaic polypeptide that is required, then the test peptide is said to specifically bind to an antibody generated to the antigenic epitope or mosaic polypeptide.

As a final determination of specificity, the pooled antisera is fully immunoabsorbed with the immunogenic peptide against which the antisera was generated until no binding to the immunogenic peptide used in the immunosorbtion is detectable. The fully immunoabsorbed antisera is then tested for reactivity with the test peptide. If no reactivity is observed, then the test peptide is specifically bound by the antisera elicited by the immunogenic protein.

Antibodies, including binding fragments and single chain recombinant versions thereof, against fragment peptides are raised by immunizing animals, e.g., using immunogenic conjugates comprising a peptide fragment covalently attached (conjugated) to a carrier proteins as described above. Typically, the immunogen of interest is a peptide of at least about three amino acids, more typically the peptide is five amino acids in length, preferably, the fragment is ten amino acids in length and more preferably the fragment is fifteen amino acids in length or greater. Often, the fragment is about twenty amino acids in length. The immunogenic conjugates are typically prepared by coupling the peptide to a carrier protein (e.g., as a fusion protein) or, alternatively, they are recombinantly expressed in an immunization vector. Antigenic determinants on peptides to which antibodies bind are typically three to ten amino acids in length.

Monoclonal antibodies are generated by methods well known to those skilled in the art and are prepared from cells secreting the desired antibody. The preferred method is a modified version of the method of Kearney, et al., *J. Immunol.* 123:1548–1558 (1979), which is incorporated by reference herein. These antibodies are screened for binding to normal or modified peptides, or screened for agonistic or antagonistic activity, e.g., activity mediated through HCV. Specific monoclonal and polyclonal antibodies will usually bind with a $K_D$ of at least about 0.1 mM, more usually at least about 50 mM, and most preferably at least approximately 1 mM or better. Often, specific monoclonal antibodies bind with a $K_D$ of 0.1 mM or better.

In some instances, it is desirable to prepare monoclonal antibodies from various mammalian hosts, such as mice, rodents, primates, humans, etc. Description of techniques for preparing such monoclonal antibodies are found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497.

Summarized briefly, this method proceeds by injecting an animal with an immunogen, i.e., an immunogenic HCV peptide of the present invention either alone or optionally linked to a carrier protein. The animal is then sacrificed and spleen cells are harvested and mixed with a myeloma cell line, such as P3X63Ag8,653. The cells are induced to fuse by the addition of polyethylene glycol. The result is a hybrid cell or "hybridoma" that is capable of reproducing in vitro. The population of hybridomas is then screened to isolate individual clones, each of which secrete a single antibody species to the immunogen. Hybridomas are chemically selected by plating the cells in a selection medium containing hypoxanthine, aminopterin and thymidine (HAT). In this manner, the individual antibody species obtained are the products of immortalized and cloned single B cells from the immune animal generated in response to a specific site recognized on the immunogenic substance. Hybridomas producing antibodies are cloned, expanded and stored frozen for future production.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The peptides and antibodies of the present invention are used with or without modification, and include chimeric antibodies such as humanized murine antibodies. Other suitable techniques involve selection of libraries of recombinant antibodies in phage or similar vectors. See, Huse et al. (1989) *Science* 246: 1275–1281; and Ward, et al. (1989) *Nature* 341: 544–546.

Techniques for the production of single chain antibodies are known to those skilled in the art and described in U.S. Pat. No. 4,946,778, which is incorporated by reference herein, and can be used to produce single chain antibodies to the peptides described herein. Bispecific antibodies, which have two antigen binding domains wherein each domain is directed against a different epitope, can also be produced.

The antibodies of the present invention can be used in affinity chromatography for isolating HCV peptides and, in addition, in isolating HCV. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified peptides are released. In addition, the antibodies can be used to screen expression libraries for particular expression products, for example, HCV proteins. Usually, the antibodies in such a procedure are labeled with a moiety allowing easy detection of presence of antigen by antibody binding. Moreover, antibodies raised against the immunogenic HCV peptides of the present invention can also be used to raise anti-idiotypic antibodies. Such antibodies are useful for detecting or diagnosing various pathological conditions related to the presence of the respective antigens.

Pharmaceutical Compositions

The antigenic epitopes and mosaic polypeptides are useful in pharmaceutical compositions, such as immunogenic compositions or vaccines, containing an immunogenic amount of the antigenic epitope, mosaic polypeptide or combinations thereof and a pharmaceutically acceptable carrier. The pharmaceutical compositions are administered to humans or animals to prevent, minimize or reduce HCV infection, particularly to patients who have been exposed to HCV or to individuals, such as health care workers or blood products recipients, who are more likely to become exposed to HCV infection. The immunogenic compositions are suitable for single administrations or a series of administrations. When given as a series, inoculations subsequent to the initial administration are given to boost the immune response and are typically referred to as booster inoculations.

One or more of the antigenic epitopes or mosaic polypeptides can be formulated and packaged, alone or in combination with other antigens, using methods and materials known to those skilled in the art for immunogenic compositions and vaccines. The immunological response may be used therapeutically or prophylactically and may provide antibody immunity or cellular immunity such as that produced by T lymphocytes such as cytotoxic T lymphocytes (CTL) or $CD4^+$ T lymphocytes.

Preferably the antigenic epitope or mosaic polypeptide is linked, coupled or conjugated to a suitable carrier molecule to enhance immunogenicity. Suitable carrier proteins include, but are not limited to, albumin, particularly human serum albumin or bovine serum albumin (BSA); hemocyanin, particularly keyhole limpet hemocyanin (KLH); thyroglobulin and derivatives thereof; polysaccharides, carbohydrates, polymers, and solid phases, such as tetanus toxoid, polyamino acids such as poly(D-lysine:D-glutamic acid), influenza, hepatitis B virus core protein, and hepatitis B virus recombinant vaccine. Other protein derived or non-protein derived substances are known to those skilled in the art.

An immunogenic carrier typically has a molecular weight of at least 1,000 daltons, preferably greater than 10,000 daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

The carrier to which the antigenic epitope or mosaic polypeptide may be conjugated may also be a polymeric delayed release system. Synthetic polymers are particularly useful in the formulation of a vaccine to effect the controlled release of antigens. For example, the polymerization of methyl methacrylate into spheres having diameters less than one micron has been reported. Microencapsulation of the antigenic epitope or mosaic polypeptide will also give a controlled release. A number of factors contribute to the selection of a particular polymer for microencapsulation.

The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly (d,l-lactide-co-glycolide) (PLGA) and other biodegradable polymers.

The immunogenic compositions can also contain a physiologically tolerable, or acceptable, diluent such as water, phosphate buffered saline, or saline, and further typically include an adjuvant. The formulation should be appropriate for the mode of administration. Adjuvants such as incomplete Freund's adjuvant, aluminum phosphate, aluminum hydroxide, or alum are materials well known in the art. The antigenic epitopes or mosaic polypeptides may be administered with an adjuvant in an amount effective to enhance the immunogenic response. At this time, the only adjuvant widely used in humans has been alum (aluminum phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the conjugate within a proteoliposome as described by Miller et al., *J. Exp. Med.* 176: 1739–1744 (1992) and incorporated by reference herein, and encapsulation of the protein in lipid vesicles such as Novasome™ lipid vesicles (Micro Vescular Systems, Inc., Nashua, N.H.) may also be useful.

The term "vaccine" as used herein includes DNA vaccines in which the nucleic acid molecule encoding antigenic epitope or mosaic polypeptide in a pharmaceutical composition is administered to a patient. For genetic immunization, suitable delivery methods known to those skilled in the art include direct injection of plasmid DNA into muscles (Wolff et al., *Hum. Mol. Genet.* 1:363 (1992)), delivery of DNA complexed with specific protein carriers (Wu et al., *J. Biol. Chem.* 264:16985 (1989), coprecipitation of DNA with calcium phosphate (Benvenisty and Reshef, *Proc. Natl. Acad. Sci.* 83:9551 (1986)), encapsulation of DNA in liposomes (Kaneda et al., *Science* 243:375 (1989)), particle bombardment (Tang et al., *Nature* 356:152 (1992) and Eisenbraun et al., *DNA Cell Biol.* 12:791 (1993)), and in vivo infection using cloned retroviral vectors (Seeger et al., *Proc. Natl. Acad. Sci.* 81:5849 (1984)).

The immunogenic compositions are intended for parenteral, topical, oral or local administration. Preferably, the immunogenic compositions are administered parenterally, such as intravenously, subcutaneously, intradermally, intranasally intraperitoneally, or intramuscularly. Thus, the immunogenic compositions provide compositions for parenteral administration that comprise a solution of the agents described above dissolved or suspended in an acceptable carrier, preferably an aqueous carrier. A variety of aqueous carriers may be used, e.g., water, buffered water, 0.4% saline, 0.3% glycine, dextrose, glycerol, ethanol, hyaluronic acid and the like and other therapeutic compounds. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the antigenic epitopes or mosaic polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The amount administered to the patient will vary depending upon what is being administered, the state of the patient and the manner of administration. In therapeutic applications, compositions are administered to a patient already suffering from HCV in an amount sufficient to inhibit spread of the virus, or at least partially arrest the symptoms of the disease and its complications. An amount adequate to accomplish this is defined as "therapeutically effective dose." Amounts effective for this use will depend on the severity of the disease, the particular composition, and the weight, age, metabolism, and general state of the patient. Generally, the dose will be in the range of about 1 mg to about 5 mg per day, preferably about 100 mg per day, for a 70 kg patient.

Vaccine compositions containing the antigenic epitopes, mosaic polypeptides and nucleic acids are administered to a patient to elicit a protective immune response against the polypeptide. A "protective immune response" is one which prevents or inhibits the spread of HCV and, thus, at least partially prevent the symptoms of the disease and its complications. An amount sufficient to accomplish this is defined as an "immunogenically effective dose." Amounts effective for this use will depend on the composition, the manner of administration, the weight and general state of health of the patient, and the judgment of the prescribing physician. For peptide compositions, the general range for the initial immunization (that is for therapeutic or prophylactic administration) is from about 100 mg to about 1 gm of peptide for a 70 kg patient, followed by boosting dosages of from about 100 mg to about 1 gm of the peptide pursuant to a boosting regimen over weeks to months depending upon the patient's response and condition, e.g., by measuring levels of HCV in the patient's blood. For nucleic acids, typically 30–1000 mg of nucleic acid is injected into a 70 kg patient, more typically about 150–300 mg of nucleic acid is injected into a 70 kg patient followed by boosting doses as appropriate. The vaccine may additionally contain stabilizers such as thimerosal (ethyl(2-mercaptobenzoate-S)mercury sodium salt)

(Sigma Chemical Company, St. Louis, Mo.) or physiologically acceptable preservatives.

HCV Detection Kits

Kits for the detection of HCV in a biological sample are provided. The kits contain one or more of the antigenic epitope peptides or mosaic polypeptides. The kits may optionally contain an apparatus and one or more containers for obtaining and storing the sample prior to and during analysis and suitable buffers and other reagents to facilitate analyte-antibody binding and detection. Each component of each kit may be provided in separate containers or any combination of the components may be provided in a single container.

The kits described herein may additionally contain equipment for safely obtaining the sample, a vessel for containing the reagents, a timing means, a buffer for diluting the sample, and a colorimeter, reflectometer, or standard against which a color change may be measured.

In a preferred embodiment, the reagents, including the antigenic epitope, mosaic polypeptide, or antibodies thereof, are lyophilized, most preferably in a single vessel. Addition of aqueous sample to the vessel results in solubilization of the lyophilized reagents, causing them to react. Most preferably, the reagents are sequentially lyophilized in a single container, in accordance with methods well known to those skilled in the art that minimize reaction by the reagents prior to addition of the sample. Preferably, the kit further comprises instructional materials for carrying out a diagnostic test for HCV.

The present invention is further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention or the scope of the appended claims.

EXAMPLE 1

Identification of Antigenic Regions, Production of an HCV Mosaic Polypeptide, and Immunogenicity Determination Sequences from four gene products (proteins) of the hepatitis C virus (HCV) were scanned using three different polymerase chain reaction (PCR)-based techniques to identify the most immunoreactive regions of those proteins.

The HCV core protein was scanned using an "anchored PCR" technique. In this techfoque, the forward primer was derived from one fixed site within the 5' terminal part of the HCV core gene ("anchored") and the reverse primers were derived from a different sites within the 3' terminal part of this gene. This technique yielded a set of PCR fragments that shared a common sequence at the 5' end with different sequences at the 3' end.

Two antigenic regions of the HCV NS4 protein, one comprising the cleavage site that separates NS4a and NS4b proteins (region 5-1-1) and the other region containing the very C-terminal part of the NS4b protein, were studied by using a "nested PCR" technique. For this technique, several sets of primers wee designed in such a way that when applied in PCR, a set of "nested" PCR fragments of increasing length was generated with each smaller fragment contained within a subsequence of each larger fragment.

For analysis of the entire HCV NS3 and NS5a proteins, a "PCR waliing" technique was employed. For this technique, a set of PCR primers was designed such that each PCR fragment was approximately 300 basepairs in length, and that each adjacent fragment overlapped the preceding fragment by approximately 100 basepairs.

All PCR fragments were cloned with a pGEX4-2T expression vector and expressed in *E. coli* as chimeric proteins with glutathione S-transferase. All proteins were tested for antigenic reactivity using a pool of anti-HCV sera by immunoblot analysis.

Those proteins demonstrating strong antigenic reactivity were selected for further analysis by enzyme immunoassay (EIA) against a panel of 160 anti-HCV positive and 160 anti-HCV-negative serum specimens to identify the most immunoreactive and specific proteins. For this, proteins were purified from crude lysates of transformed bacterial cells using ligand affinity chromatography.

The most diagnostically relevant proteins identified in this example were as follows:

1) Core protein: clone #24-4 containing amino acid residues 1–91 of the HCV (genotype 1b) polyprotein (SEQ ID NO: 1):

MSTNPKPQRKTKRNTNRRPQDVKFPGGG-QIVGGVYLLPRR GPRLGVRATRKTSERSQPRGR-RQPIPKARRPEGRTWAQPGY PWPLYGNEGM

2) NS3 protein: clone #16 containing amino acid residues 1471–1573 of the HCV (genotype 1b) polyprotein (SEQ ID NO:2):

VPHPNIEEVALSNTGEIPFYGKAIP-IEAIKGGRHLIFCHSKKKC DELAAKLT-GLGLNAVAYYRGLDVSVIPTSGDVVVATDALM TGFTGDFDSVIDCNTCVT

3) NS4 protein (region 5-1-1): clone #25-3 containing amino acid residues 1789–1867 of the HCV (genotype 1b) polyprotein (SEQ ID NO:3):

SVVIVGRIILSGRPAVIPDREVLYQEF-DEMEECASHLPYIEQG MQLAEQFKQKAL-GLLQTATKQAEAAAPVVESKWRAL

4) NS4 protein (region 59: clone #26-4 containing amino acid residues 1916–1948 of the HCV (genotype 1b) polyprotein (SEQ ID NO:4):

MNRLIAFASRGNHVSPTHYVPESDAAARVTQIL

5) NS5a protein: clone #35 containing amino acid residues 2322–2423 of the HCV (genotype 1b) polyprotein (SEQ ID NO:5):

KATCTTHHDSPDADLIEANLLWRQEMGG-NITRVESENKVVI LDSFDPIRAVEDEREISVPAEIL-RKPRKFPPALPIWARPDYNP PLLESWKDPDYVPPV-VHG

Several artificial composite proteins, or mosaic polypeptides, were designed based on this analysis. The first mosaic polypeptide was composed of one antigenic region each from core, NS3 and NS4. The second protein contained an additional NS4 region, while the third contained all immunodominant antigenic regions identified in this example.

DNA fragments derived from clone #24-4, #16, and #25-3 containing HCV-specific sequences were joined together by PCR to produce a J-gene encoding for a protein containing sequences of the HCV core (1–91 aa), NS3 (1471–1573 aa), and NS4 region 5-1-1 (1789–1867 aa). This fragment was cloned with the same expression vector pGEX4-2T, purified by ligand chromatography and analyzed for antigenic reactivity.

Another hybrid gene designated J+26-4 was constructed by adding a DNA fragment encoding for the NS4 59 region (1916–1948 aa). This gene was also expressed in *E. coli* and analyzed for antigenic reactivity.

A third hybrid, designated the T-gene, was constructed by adding to the J+26-4 gene a DNA fragment encoding for the NS5a segment (2322–2423 aa). The T protein was expressed at high yield in *E. coli*, purified from crude lysates and analyzed with a panel of anti-HCV positive and negative sera by enzyme immunoassay (EIA).

The EIA analysis demonstrated that each mosaic protein gave nearly identical results when compared to combining each of the corresponding individual proteins.

Modifications and variations of the present invention will be obvious to those skilled in the art from the foregoing detailed description. Such modifications and variations are intended to come within the scope of the appended claims.

The entire text of the references mentioned herein are hereby incorporated in their entireties by reference.

We claim:

1. A mosaic polypeptide comprising an isolated antigenic epitope of HCV NS3 protein, wherein the antigenic epitope is amino acid residues 1471–1573 of the HCV polyprotein set forth in SEQ ID NO:2.

2. An assay for detecting HCV in a biological sample comprising combining the biological sample with an HCV reagent for a sufficient amount of time under conditions to form an analyte-antibody complex and detecting the complex, wherein the HCV reagent is a mosaic polypeptide comprising an antigenic epitope of the NS3 protein, wherein the antigenic epitope of the NS3 protein consists of amino acid residues 1471–1573 of the HCV polyprotein (SEQ ID NO:2), wherein detection of the analyte-antibody complex indicates that thebiological sample contains HCV.

3. An immunogenic composition comprising an immunogenic amount of a mosaic polypeptide of claim 1 and a pharmaceutically acceptable carrier.

4. The immunogenic composition of claim 3 wherein the mosaic polypeptide further comprises one or more antigenic epitopes selected from the group consisting of amino acid residues 1–91 of the HCV polynrotein (SEQ ID NO:1), amino acid residues 1789–1867 of the HCV polyprotein (SEQ ID NO:3), amino acid residues 19 16–1948 of the HCV polyprotein (SEQ ID NO:4) and amino acid residues 2322–2423 of the HCV polyprotein (SEQ ID NO:5).

5. The mosaic polypeptide of claim 1 comprising amino acid residues of the HCV polyprotein wherein the amino acid sequence comprises SEQ ID NOS:1–5.

6. The mosaic polypeptide of claim 1, wherein the mosaic polypeptide is not the HCV polyprotein.

7. The mosaic polypeptide of claim 1, further comprising one or more antigenic epitopes selected from the group consisting of amino acid residues 1–91 of the HCV polyprotein (SEQ ID NO:1), amino acid residues 1789–1867 of the HCV polyprotein (SEQ ID NO:3), amino acid residues 1916–1948 of the HCV polyprotein (SEQ ID NO:4) and amino acid residues 2322–2423 of the HCV polyprotein (SEQ ID NO:5).

8. The assay of claim 2, wherein the mosaic polypeptide further comprises one or more antigenic epitopes selected from the group consisting of amino acid residues 1–91 of the HCV polyprotein (SEQ ID NO:1), amino acid residues 1789–1867 of the HCV polyprotein (SEQ ID NO:3), amino acid residues 1916–1948 of the HCV polyprotein (SEQ ID NO:4) and amino acid residues 2322–2423 of the HCV polyprotein (SEQ ID NO:5).

* * * * *